US00PP14621P29

(12) United States Plant Patent
Fransen

(10) Patent No.: US PP14,621 P2
(45) Date of Patent: Mar. 23, 2004

(54) LIGULARIA PLANT NAMED 'LITTLE ROCKET'

(50) Latin Name: *Ligularia Hybrida*
Varietal Denomination: Little Rocket

(75) Inventor: Marco J. W. Fransen, Ter Aar (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/437,957

(22) Filed: May 13, 2003

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Database, GTI Jouve Retrieval Software 2003/04 Citation(s) for 'Little Rocket'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Ligularia plant named 'Little Rocket', characterized by its upright, somewhat outwardly spreading and relatively compact plant habit; freely basal branching growth habit; freely flowering habit; and yellow-colored ray and disc florets.

2 Drawing Sheets

Botanical classification/cultivar designation: *Ligularia Hybrida* cultivar Little Rocket.

BACKGROUND OF THE INVENTION

The present Invention relates to a new and distinct cultivar of Ligularia plant, botanically known as *Ligularia Hybrida*, and hereinafter referred to by the name 'Little Rocket'.

The new Ligularia is a product of a planned breeding program conducted by the Inventor in Ter Aar, The Netherlands. The objective of the breeding program is to create new Ligularia cultivars that are more compact.

The new Ligularia originated from a cross-pollination made by the Inventor in Ter Aar, The Netherlands of a proprietary seedling selection originating from a cross-pollination of the Ligularia cultivar Laternchen and the Ligularia cultivar The Rocket, not patented, as the female, or seed, parent with the Ligularia cultivar The Rocket, not patented, as the male, or pollen, parent. The new Ligularia was discovered and selected by the Inventor as a single flowering plant within the progeny of the stated cross grown in a controlled environment in Ter Aar, The Netherlands, in 1999.

Asexual reproduction of the new Ligularia by divisions was first conducted in Ter Aar, The Netherlands in 2000. Since then, asexual reproduction by divisions has shown that the unique features of this new Ligularia are stable and reproduced true to type in successive generations.

SUMMARY OF THE INVENTION

The cultivar Little Rocket has not been observed under all possible environmental conditions. The phenotype may vary somewhat with variations in environment such as temperature and light intensity without, however, any variance in genotype.

The following traits have been repeatedly observed and are determined to be the unique characteristics of 'Little Rocket'. These characteristics in combination distinguish 'Little Rocket' as a new and distinct Ligularia:

1. Upright, somewhat outwardly spreading and relatively compact plant habit.
2. Freely basal branching growth habit.
3. Freely flowering habit.
4. Yellow-colored ray and disc florets.

Plants of the new Ligularia differ primarily from plants of the parents in plant height and floriferousness as plants of the parents are not as compact and not as freely flowering as plants of the new Ligularia.

Plants of the new Ligularia can also be compared to plants of the Ligularia cultivar Papillon, not patented. However, plants of the new Ligularia are more compact and have more inflorescences per basal stem than plants of the cultivar Papillon.

BRIEF DESCRIPTION OF THE PHOTOGRAPHS

The accompanying colored photographs illustrate the overall appearance of the new Ligularia showing the colors as true as it is reasonably possible to obtain in colored reproductions of this type. Colors in the photographs may differ from the color values cited in the detailed botanical description which accurately describe the colors of the new Ligularia.

The photograph on the first sheet comprises a side perspective view of a typical flowering plant of 'Little Rocket' grown in an outdoor nursery.

The photograph at the top of the on the second sheet comprises a close-up view of a typical inflorescence of 'Little Rocket'.

The photograph at the bottom of the second sheet comprises a close-up view of a typical leaf of 'Little Rocket'.

DETAILED BOTANICAL DESCRIPTION

The aforementioned photographs and following observations and measurements describe plants grown in Lisserbroek, The Netherlands, in an outdoor nursery under full sun conditions. In July, when plants were about two years old, the photographs and the observations and measurements were taken. During this time, day temperatures ranged from 14 to 27° C. and night temperatures ranged from 7 to 14° C. Color references are made to The Royal Horticultural Society Colour Chart, 2001 edition, except where general terms of ordinary dictionary significance are used.

Botanical classification: *Ligularia Hybrida* cultivar Little Rocket.

Parentage:

*Female, or seed, parent.*—Proprietary seedling selection originating from a cross-pollination of the Ligularia cultivar Laternchen (unpatented) and the Ligularia cultivar The Rocket, not patented.

*Male, or pollen, parent.*—Ligularia cultivar The Rocket, not patented.

Propagation:

*Type.*—By divisions.

*Root description.*—Fine, freely-branching; light brown to white in color.

Plant description:

*Appearance.*—Perennial herbaceous container and garden plant. Upright and somewhat outwardly spreading plant habit; inverted triangle. Freely basal branching; about 15 basal branches per plant. Vigorous growth habit.

*Plant height.*—About 120 cm.

*Plant width or area of spread.*—About 120 cm.

*Basal branches.*—Length: About 120 cm. Diameter: About 1 cm. Internode length: About 14.5 cm. Aspect: Upright to slightly outward. Strength: Strong. Texture: Sparsely pubescent. Color: 200A with longitudinal stripes, 141A.

*Foliage description.*—Arrangement: Basal and stem leaves, alternate; single. Length: Basal leaves: About 28 cm. Stem leaves: About 21 cm. Width: Basal leaves: About 34 cm. Stem leaves: About 24 cm. Shape: Roughly palmate. Apex: Acute. Base: Hastate. Margin: Dentate to bidentate lobes. Venation pattern: Palmate. Texture, upper and lower surfaces: Slightly rough; veins furrowed; sparsely pubescent. Color: Developing foliage, upper surface: Between 137A and 139A. Developing foliage, lower surface: 137C to 137D. Fully expanded foliage, upper surface: Closest to N189A. Fully expanded foliage, lower surface: 137C. Venation, upper and lower surfaces: N186C. Petiole: Length: About 16 cm. Diameter: About 6 mm. Texture, upper and lower surfaces: Smooth. Color, upper and lower surfaces: 200B to 200C with longitudinal stripes, 137A.

Inflorescence description:

*Appearance.*—Composite inflorescence form; inflorescences arranged on mostly erect racemes; inflorescences radial and facing upright to outwardly. Inflorescences persistent.

*Flowering response.*—Plants flower continuous and freely from mid-June to late July in Lisserbroek, The Netherlands.

*Postproduction longevity.*—Inflorescences maintain good color and substance for about seven days on the plant when grown in an outdoor environment.

*Quantity of inflorescences.*—Freely flowering; about 150 open and developing inflorescences per basal branch.

*Fragrance.*—Moderate; musty, unpleasant.

*Inflorescence bud.*—Length: About 1.1 cm. Diameter: About 4 mm. Shape: Ovoid. Color: 200A to N200A; towards the apex, 13A to 14B.

*Inflorescence size.*—Diameter: About 63 cm. Depth (height): About 6.2 cm.

*Ray florets.*—Quantity per floret: One. Length: About 1.5 cm. Width: About 5 mm. Shape: Oblanceolate. Apex: Retuse to praemorse. Base: Attenuate. Margin: Entire. Texture, upper and lower surfaces: Smooth. Color, when opening and fully opened, upper and lower surfaces: 14A.

*Disc florets.*—Quantity per inflorescence: Five. Length: About 6 mm. Width: About 1 mm. Shape: Narrowly oblong; lower half fused into a tube. Apex: Obtuse. Base: Fused. Margin: Entire. Texture, upper and lower surfaces: Smooth. Color, when opening and fully opened, upper and lower surfaces: 13A.

*Involucral bracts.*—Quantity per inflorescence: Five. Length: About 1 cm. Diameter: About 1.5 mm. Shape: Narrowly oblong. Apex: Acute. Margin: Entire. Color, upper and lower surfaces: 137A; towards the apex, 200A to 200B.

*Pedicels.*—Length: About 1.3 cm. Diameter: About 1.5 mm. Angle: About 30 to 50° from vertical. Strength: Strong. Color: N200A.

*Reproductive organs.*—Androecium: Stamen quantity per floret: Five per floret; basifixed. Anther shape: Narrowly elliptic. Anther length: About 4 mm. Anther color: 199B. Filament length: About 5 mm. Filament color: 6A. Pollen amount: None detected. Gynoecium: Pistil quantity per floret: One. Pistil length: About 1 cm. Stigma shape: Two-parted; cleft. Stigma color: 14A. Style length: About 9 mm. Style color: 14B. Ovary color: 145A to 145B.

*Fruit.*—Type: Achene. Quantity per basal branch: About 2,550. Length: About 1.4 mm. Diameter: About 6 mm. Texture: Pubescent. Color: 199A to N200A.

*Seed.*—Quantity per fruit: One. Length: About 8 mm. Diameter: About 1 mm. Color: 199A to N200A.

Disease/pest resistance: Resistance to pathogens and pests common to Ligularias has not been observed on plants grown under outdoor conditions.

Temperature tolerance: Plants of the new Ligularia have been observed to tolerate temperatures from about −30 to 40° C.

It is claimed:

1. A new and distinct cultivar of Ligularia plant named 'Little Rocket', as illustrated and described.

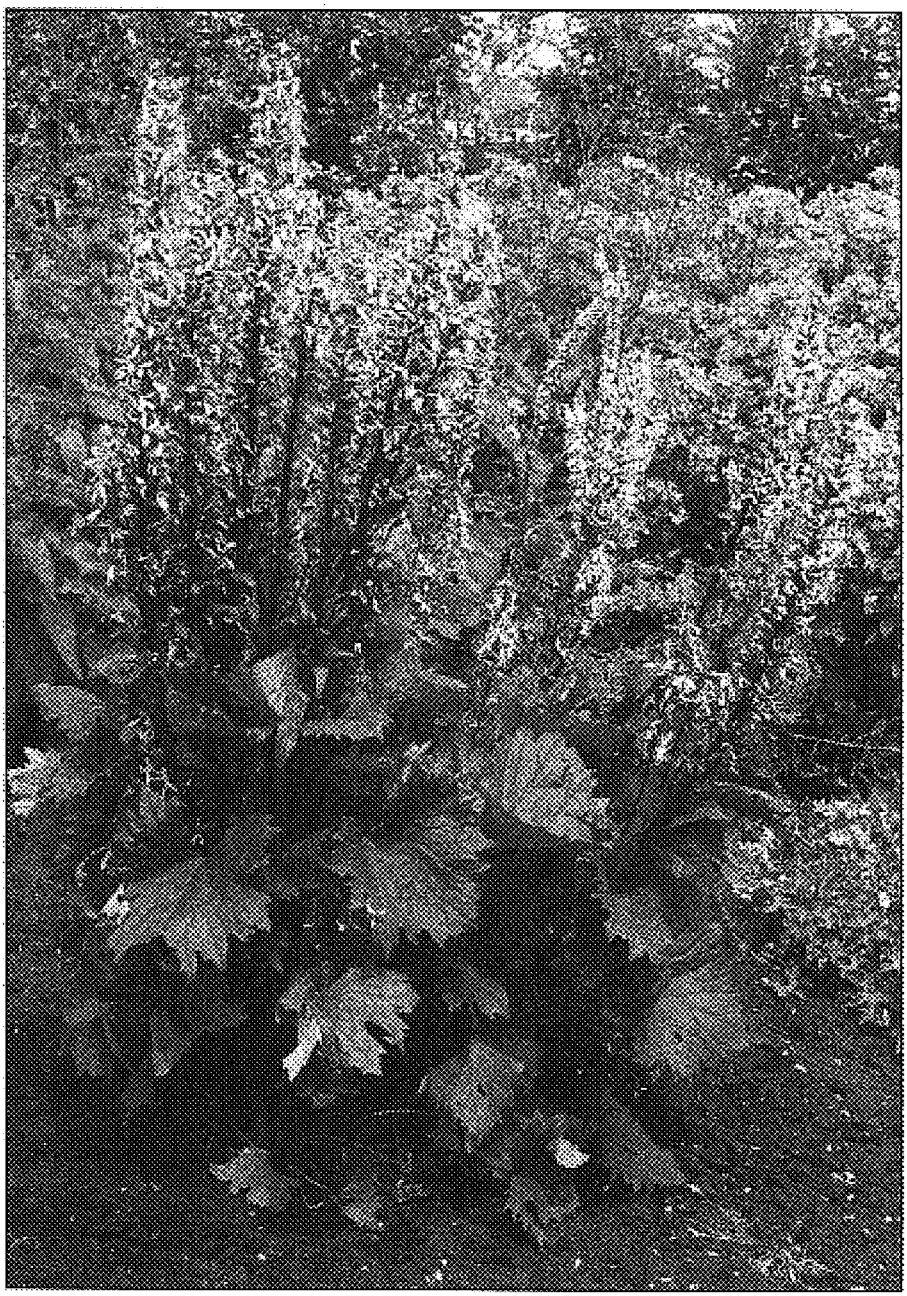

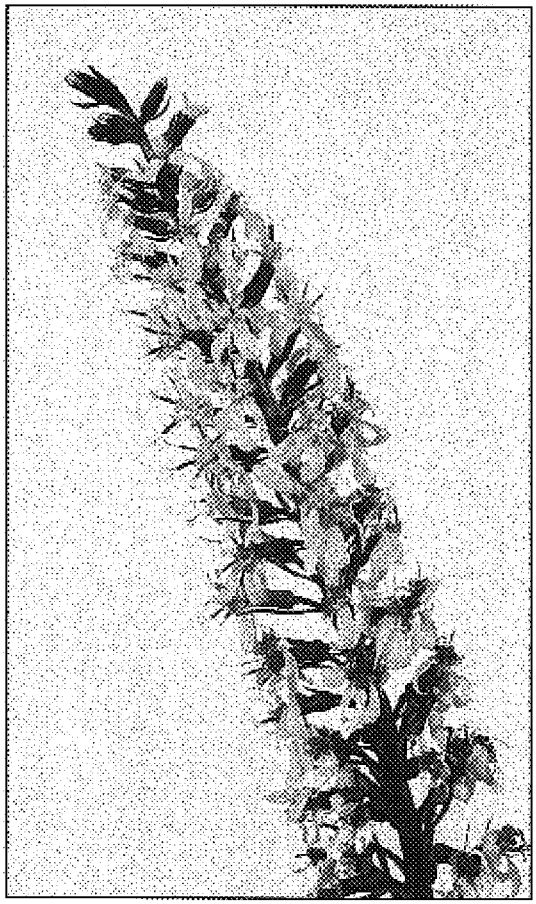
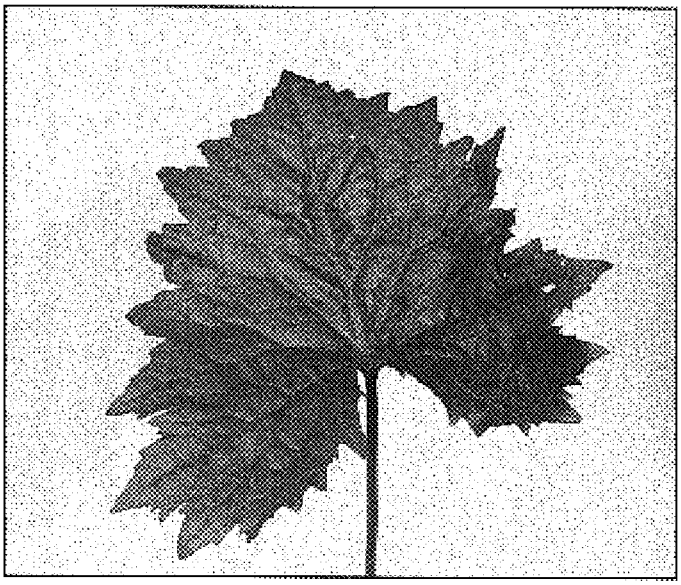

* * * * *